(12) United States Patent
Kuo

(10) Patent No.: US 9,642,678 B2
(45) Date of Patent: May 9, 2017

(54) METHOD AND SYSTEM FOR DENTAL VISUALIZATION

(75) Inventor: Eric Kuo, Foster City, CA (US)

(73) Assignee: Align Technology, Inc., San Jose, CA (US)

( * ) Notice: Subject to any disclaimer, the term of this patent is extended or adjusted under 35 U.S.C. 154(b) by 798 days.

(21) Appl. No.: 12/346,719

(22) Filed: Dec. 30, 2008

(65) Prior Publication Data

US 2010/0167225 A1 Jul. 1, 2010

(51) Int. Cl.
| | | |
|---|---|---|
| *G06G 7/48* | (2006.01) | |
| *A61C 7/08* | (2006.01) | |
| *G06F 17/50* | (2006.01) | |
| *A61C 7/00* | (2006.01) | |

(52) U.S. Cl.
CPC ............ *A61C 7/08* (2013.01); *G06F 17/5009* (2013.01); *A61C 7/002* (2013.01)

(58) Field of Classification Search
CPC .. A61C 7/08; A61C 7/002; A61C 7/00; G06F 17/5009; G06F 17/50
USPC ........................................ 703/6, 2; 433/6, 24
See application file for complete search history.

(56) References Cited

U.S. PATENT DOCUMENTS

| | | | |
|---|---|---|---|
| 5,975,893 A | | 11/1999 | Chishti et al. |
| 6,217,325 B1 * | | 4/2001 | Chishti et al. .................. 433/24 |
| 6,688,885 B1 * | | 2/2004 | Sachdeva et al. .............. 433/24 |
| 6,733,289 B2 * | | 5/2004 | Manemann et al. ............ 433/24 |
| 7,074,038 B1 * | | 7/2006 | Miller .............................. 433/24 |
| 7,306,152 B2 * | | 12/2007 | Culp et al. ............... 235/462.01 |
| 7,930,189 B2 | | 4/2011 | Kuo |
| 2004/0013993 A1 * | | 1/2004 | Ito ..................................... 433/6 |
| 2005/0038669 A1 * | | 2/2005 | Sachdeva et al. ................ 705/2 |
| 2005/0192835 A1 * | | 9/2005 | Kuo et al. ......................... 705/2 |
| 2007/0129991 A1 * | | 6/2007 | Kuo ................................ 705/10 |
| 2007/0168152 A1 * | | 7/2007 | Matov et al. ................. 702/155 |
| 2009/0191502 A1 * | | 7/2009 | Cao et al. ....................... 433/24 |
| 2009/0246726 A1 * | | 10/2009 | Chelnokov et al. ............ 433/24 |

OTHER PUBLICATIONS

Sarver, David M. et al., "Dynamic Smile Visualization and Quantification: Part 2. Smile Analysis and Treatment Strategies", 2003, American Association of Orthodontists.*
Rodrigues, Maria Andreia F. et al., "An Interactive Simulation System for Training and Treatment Planning in Orthodontics", Apr. 15, 2007, Elsevier Ltd.*
Alcaniz, Mariano et al. "An Advanced System for the Simulation and Planning of Orthodontic Treatment", Oct. 16, 1997, Oxford University Press.*

(Continued)

*Primary Examiner* — Cedric D Johnson

(57) ABSTRACT

In particular embodiments, method, apparatus and system for receiving digital representations of the initial parameters of a dentition; simulating a first orthodontic treatment process on the digital representations of the initial parameters, displaying a set of output results from the simulation of the first orthodontic treatment process, simulating a second orthodontic treatment process on the output results from the simulation of the first orthodontic treatment process, and displaying a set of output results from the simulation of the second orthodontic treatment process are provided.

34 Claims, 12 Drawing Sheets

(56) References Cited

OTHER PUBLICATIONS

Li, Chengjun et al. "Orthodontic Simulation and Diagnosis: An Enhanced Tool for Dentists", Sep. 1-4, 2005, IEEE Engineering in Medicine and Biology, 27th Annual Conference.*
Lapatki, B.G. et al., "Smart Bracket for Multi-Dimensional Force and Moment Measurement", 2007, Research Reports Biomaterials & Bioengineering, J Dent Res 86 (1), International and American Associations for Dental Research.*

* cited by examiner

METHOD AND SYSTEM FOR DENTAL VISUALIZATION

BACKGROUND

The present disclosure relates generally to the field of dentistry. More specifically, the present disclosure relates to the field of virtual orthodontic treatment planning and visualization.

One main objective of orthodontics is to move a patient's teeth into an optimal target occlusion, or a position in which the teeth function optimally and are aesthetically pleasing to the patient. Conventionally, appliances such as braces, which are a bracket and arch wire system, are applied to the teeth of the patient by an orthodontist or other qualified dental professional. The brackets in the braces system are mounted on the surface of the teeth of a patient and the arch wire couples all the brackets on the same jaw to one another. The arch wire is incrementally tightened over time during office visits to the treating professional, exerting a continual force on the teeth, gradually moving them toward a desired target position.

Recently, a system for treating dental malocculsions has become available under the trade name Invisalign® System. The Invisalign® System has two components. The first component is called ClinCheck® and allows practitioners to simulate treatment of teeth by observing and modeling two-week stages of tooth movement. Based on the results of the ClinCheck® component, the second component comprises aligners which are thin, clear, plastic removable dental appliances that correspond to each treatment stage of the ClinCheck® simulation. The aligners are manufactured using advanced computer-controlled fabrication systems. Each aligner is worn by the patient for approximately two weeks before it is exchanged for a next stage aligner intended to further reposition the teeth. The Invisalign® System addresses many of the significant limitations of conventional braces. In particular, the Invisalign® System aligners are virtually invisible, and are therefore more ascetically pleasing for the patient. Second, the aligners are generally less painful and uncomfortable than are traditional braces. Additionally, the aligners can be removed to permit conventional oral hygiene, thus being more healthy for the patient's teeth.

SUMMARY

Embodiments of the present disclosure in one aspect includes receiving digital representations of the initial parameters of a dentition, simulating a first orthodontic treatment process on the digital representations of the initial parameters, displaying a set of output results from the simulation of the first orthodontic treatment process, simulating a second orthodontic treatment process on the output results from the simulation of the first orthodontic treatment process, and displaying a set of output results from the simulation of the second orthodontic treatment process.

A computer program product in another aspect includes a medium readable by a computer, the computer readable medium having computer program code adapted to receive digital representations of the initial parameters of a dentition, simulate a first orthodontic treatment process on the digital representations of the initial parameters, display a set of output results from the simulation of the first orthodontic treatment process, simulate a second orthodontic treatment process on the output results from the simulation of the first orthodontic treatment process, and display a set of output results from the simulation of the second orthodontic treatment process.

DETAILED DESCRIPTION

Figure 1A:
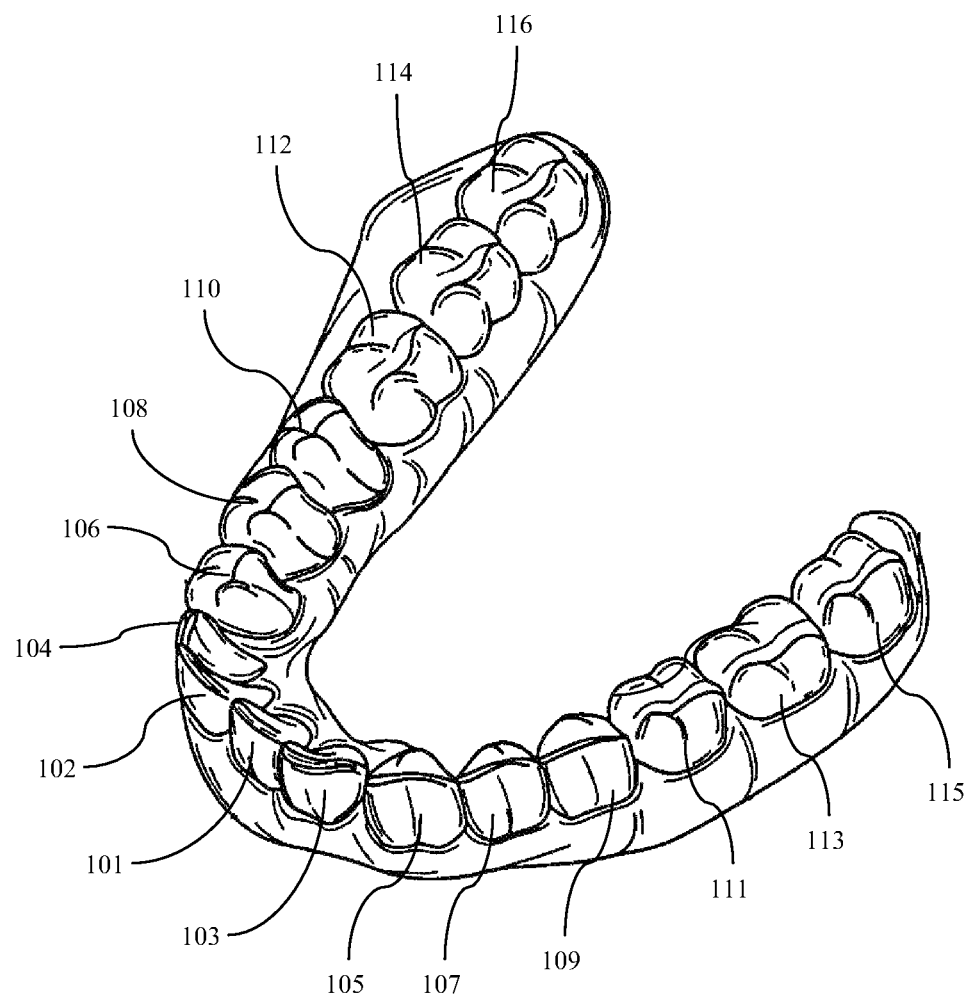
FIG. 1A is a diagram of the lower jaw and teeth of a patient's mouth.

FIG. 1 is a diagram of the lower jaw and teeth of a patient's mouth. Referring to FIG. 1, the lower jaw 100 of a patient may include teeth such as the left central incisor 101, the right central incisor 102, the left lateral incisor 103, the right lateral incisor 104, the left cuspid or canine 105, the right cuspid 106, the left first bicuspid 107, the right first bicuspid 108, the left second bicuspid 109, the right second bicuspid 110, the left first molar 111, the right first molar 112, the left second molar 113, the right second molar 114, the left third molar or wisdom tooth 115, and the right third molar or wisdom tooth 116. The upper jaw of a patient may have a similar set of incisors, cuspids, bicuspids, and molars. The relationship between the individual teeth of the jaw 100 and the relationship between the sets of teeth on the upper and lower jaws 100 are used to determine the corrective measures needed in a chosen orthodontic procedure. Different types of malocclusion, a non-optimal positioning of a patient's teeth, may include, among others, overbite, also known as class 11 malocclusion, underbite, also known as class III malocclusion, overjet, and diastema. Individual teeth position may also affect the type of chosen orthodontic procedure, such as crooked or rotated teeth.

Figure 1B:
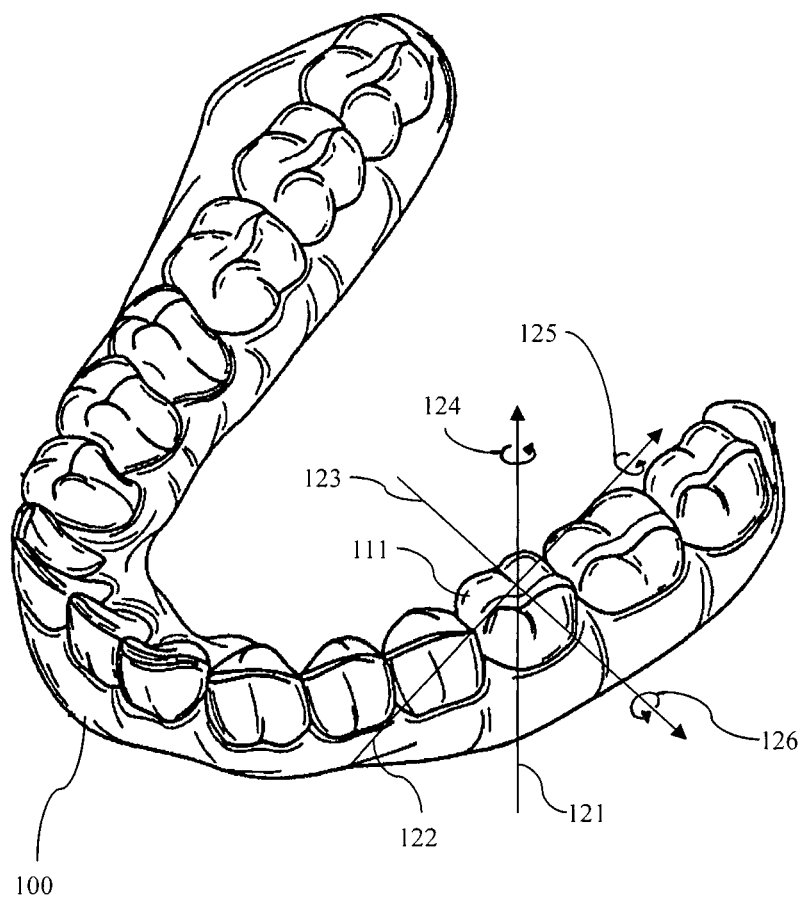
FIG. 1B illustrates a patient's jaw and provides a general indication of how teeth may be moved.
Figure 1C:
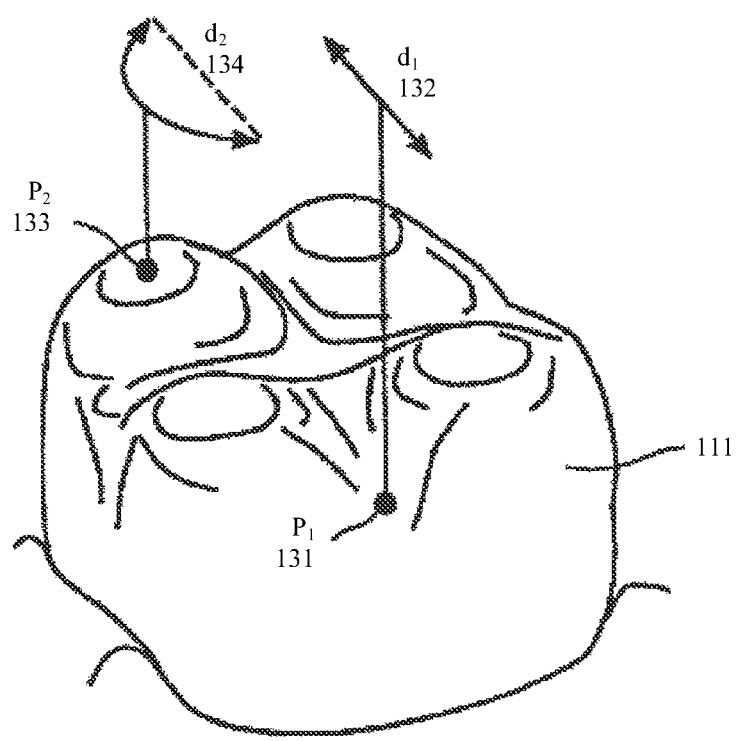
FIG. 1C illustrates a single tooth and illustrates how tooth movement distances may be determined.

FIG. 1B illustrates a patient's jaw and provides a general indication of how teeth may be moved and FIG. 1C illustrates a single tooth and illustrates how tooth movement distances may be determined. Referring to FIG. 1B, a representative jaw 100 includes a plurality of teeth. To understand how the teeth may be moved, an arbitrary centerline 121 is drawn through one of the teeth 111. With reference to this centerline, the tooth may be moved in the orthogonal direction represented by axes 121-123, where 121 represents the centerline. Additionally, the tooth may be moved about the axes 121-123 as indicated by 124-126. Thus, all possible free-form motions of the tooth may be performed.

Referring now to FIG. 1C, the magnitude of any tooth movement achieved by methods and systems, may be defined in terms of the maximum linear translation of any point $P_i$ on a tooth 111. Each point $P_i$ will undergo a cumulative translation as that tooth is moved in any of the orthogonal or rotational directions defined in FIG. 1B. That is, while the point will usually follow a non-linear path, there will be a linear distance between any point in the tooth when determined at any two times during the treatment. Thus an arbitrary point $P_1$ 131 may in fact undergo a true side-to-side translation as indicated by arrow $d_1$ 132, while a second arbitrary point $P_2$ 133 may travel along an arcuate path, resulting in a target translation $d_2$ 134.

There are a number of methods of correcting malocclusion, or the poor or non-optimal positioning of the teeth of a patient. Such methods include, but are not limited to, oral surgery, elastics, removable appliances, such as polymeric shell aligners and palate expanders, and fixed orthodontic appliances, such as braces. While each method may be used individually, in some cases it may be desirable for the patient and treating dental or orthodontic professional to use a combination of two or more of the same or different aforementioned methods. Possible reasons for using a combination of two or more different treatments may be, for example, for optimizing treatment for patient comfort, time requirements, monetary cost, or optimal target result.

Figure 2:
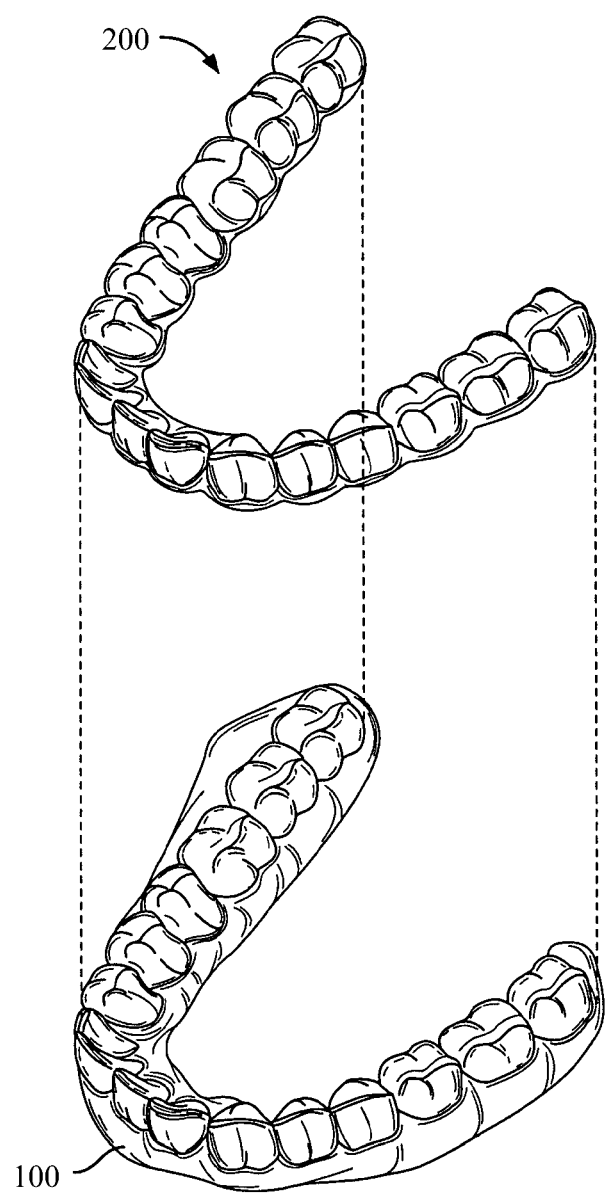
FIG. 2 illustrates an example of a non-bracket polymeric shell aligner for use in one or more embodiments of the present disclosure.

FIG. 2 illustrates an example of a non-bracket polymeric shell aligner for use in one or more embodiments of the present disclosure. Referring to FIG. 2, systems according to one or more embodiments of the present disclosure may comprise a plurality of incremental position adjustment appliances. The appliances are intended to effect incremental repositioning of individual teeth in the jaw as described generally above. A preferred appliance 200 will comprise a polymeric shell having a cavity shaped to receive and resiliently reposition teeth from one tooth arrangement to a successive tooth arrangement. The polymeric shell will preferably, but not necessarily, fit over all teeth present in the upper or lower jaw. Often, only certain one(s) of the teeth will be repositioned while others of the teeth will provide a base or anchor region for holding the repositioning appliance in place as it applies the resilient repositioning force against the tooth or teeth to be repositioned. In complex cases, however, many or most of the teeth will be repositioned at some point during the treatment. In such cases, the teeth which are moved can also serve as a base or anchor region for holding the repositioning appliance. Additionally, the gums and/or the palette can serve as an anchor region, thus allowing all or nearly all of the teeth to be repositioned simultaneously.

Referring still to FIG. 2, the polymeric appliance 200 is shaped to fit over the teeth of the jaw 100 and is preferably formed from a thin sheet of a suitable elastomeric polymeric, such as Tru-Tain 0.03 in. thermal forming dental material, Tru-Tain Plastics, Rochester, Minn. 55902. Usually, no wires or other means will be provided for holding the appliance in place over the teeth. In some cases, however, it will be desirable or necessary to provide individual anchors on teeth with corresponding receptacles or apertures in the appliance 200 so that the appliance can apply an upward or other force or torque on the tooth which would not be feasible in the absence of such an anchor.

Figure 3:
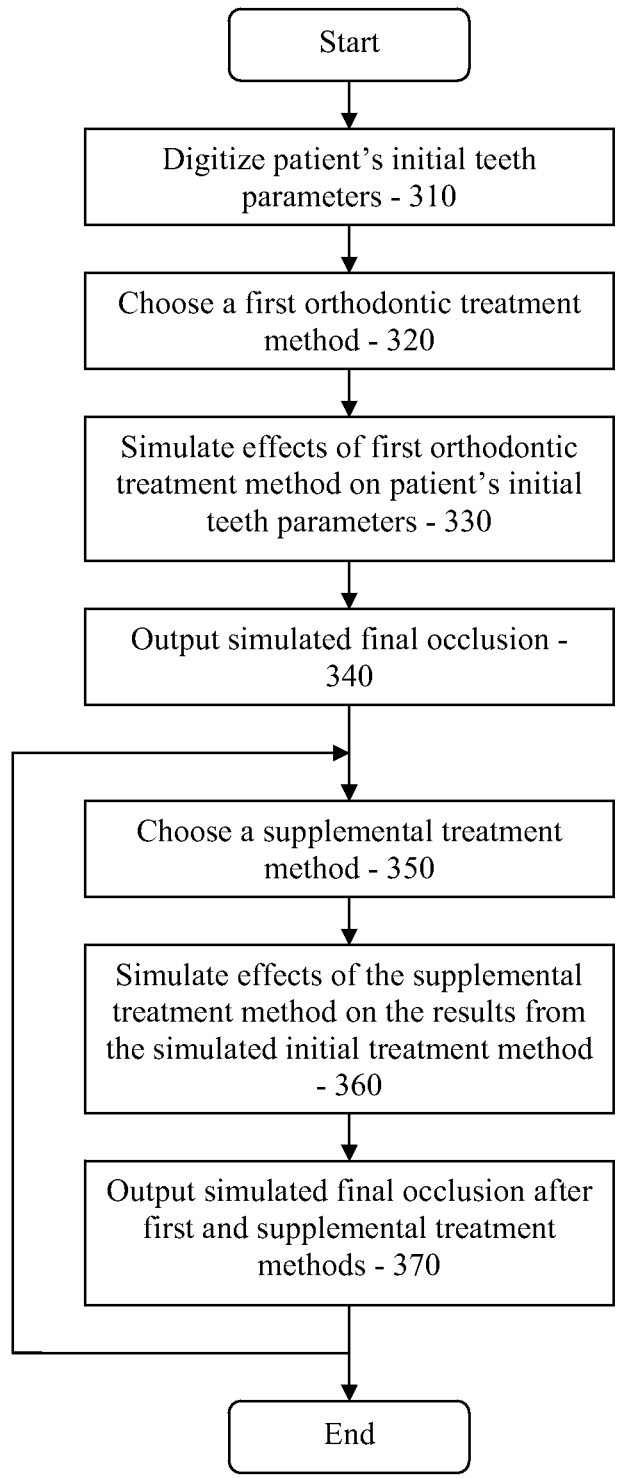
FIG. 3 illustrates a procedure for providing orthodontic treatment based on one or more treatments in one aspect.

FIG. 3 illustrates a method of treating a patient using one or more orthodontic treatments. Referring to FIG. 3, a flow chart of a method of treating a patient using one or more orthodontic treatments is shown. In one embodiment of the present disclosure, it may be advantageous to simulate the effects of a chosen method or methods of treating the malocclusion of a patient's teeth. Virtual orthodontics is a useful tool for such a simulation. Virtual orthodontics is a method of digitizing patients' initial teeth parameters and applying virtual forces representing the treatment plan on the initial teeth parameters. In one embodiment, the digitization of a patient's initial teeth parameters (310) is done by scanning the teeth and bite set of a patient. This may be done by, among others, interoral scanning, X-ray, or magnetic resonance imaging (MRI). The scan may be a direct scan of the patient's teeth, or an indirect scan, using a dental impression. The digital scan of the patient's initial teeth parameters may include, among others, views of each individual tooth, the position and geometry of each individual tooth, the relationship between neighboring teeth, a view of each individual jaw, and the entire bite set of the patient.

Still referring to FIG. 3, based on the initial tooth parameters, an orthodontist or other dental professional may choose a first treatment method (320) based on, among others, experience, preference, and patient inclination. The preferred first treatment method is the use of polymeric shell appliances, such Align Technology, Inc.'s Invisalign® appliances and those described in U.S. Pat. No. 5,975,893, however other treatment methods may include the use of fixed orthodontic appliances, such as traditional braces, oral surgery, or elastics. The digital representation of the patient's initial teeth parameters is loaded into a software program and the chosen treatment is virtually applied to the digital teeth parameters. The virtual treatment may be a virtual representation of the treatment itself, or may be a geometric representation of the forces that would be applied by the treatment.

A software algorithm is used to simulate the effects of the chosen treatment method on the patient's initial teeth parameters (330). The simulation may output a target occlusion (340), or positioning of the teeth, based on the effects of the chosen first treatment method. The output may be, among others, a visual representation, a mathematical description, or a combination thereof. The output may also display target position and rotation of one or more of, each individual tooth of the patient, the relationship between neighboring teeth, a view of each individual jaw, and the entire bite set of the patient.

A second or supplementary treatment may be chosen by the orthodontist or dental professional (350) to further correct a patient's malocclusion. The supplementary treatment may be a different treatment type than the first treatment, or a further treatment of the same treatment type. A simulation of the supplementary treatment (360) may be done using the output occlusion after the first treatment as the supplementary initial tooth parameters. A virtual representation of the supplementary treatment may be applied to the supplementary initial tooth parameters, and the target output from the application of the supplementary treatment process (370) may be displayed for viewing by the patient and treating professional. If further treatment is still desired or necessary, yet another supplementary treatment may be chosen (350) and simulated (360) and the resulting occlusion outputted (370). This process may be repeated as often as desired until the desired target occlusion may be achieved.

Figure 4:
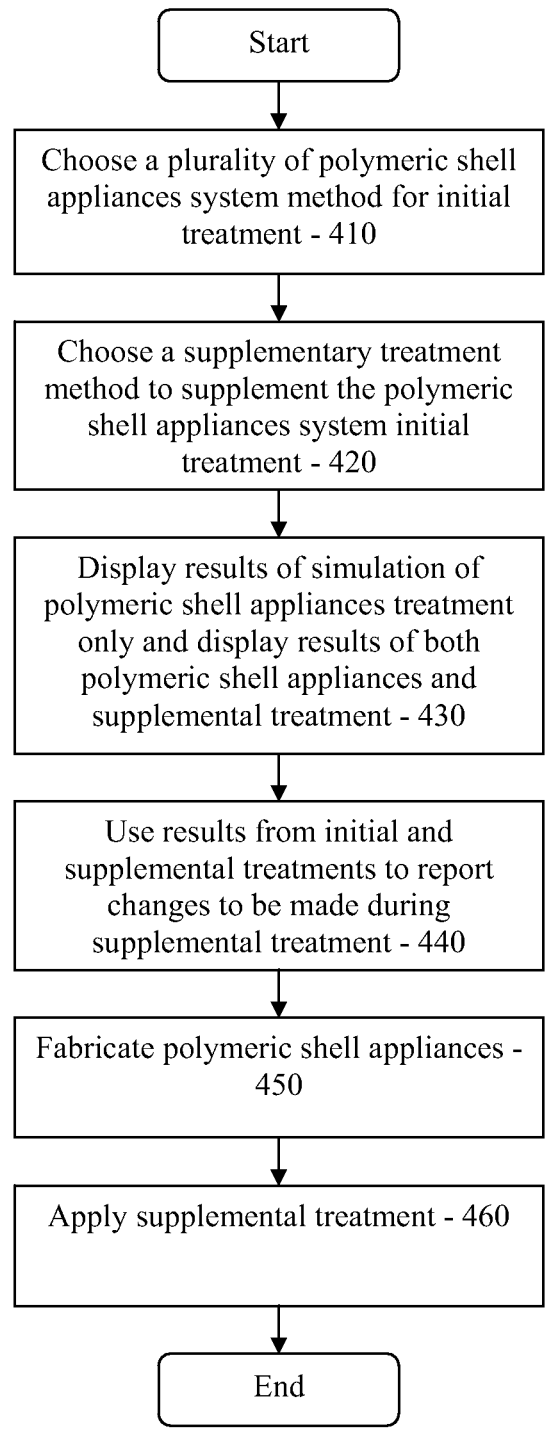
FIG. 4 illustrates a procedure for providing orthodontic treatment based on one or more treatments in another aspect.

FIG. 4 illustrates a method of treating a patient using one or more orthodontic treatments. Referring to FIG. 4, in one embodiment of the present disclosure, the initial chosen orthodontic procedure may include a plurality of polymeric shell aligner appliances (410), such as Align Technology, Inc.'s Invisalign® appliances. The initial orthodontic procedure is shown in FIGS. 5 and 6 of the present disclosure and described in detail below.

Figure 5:
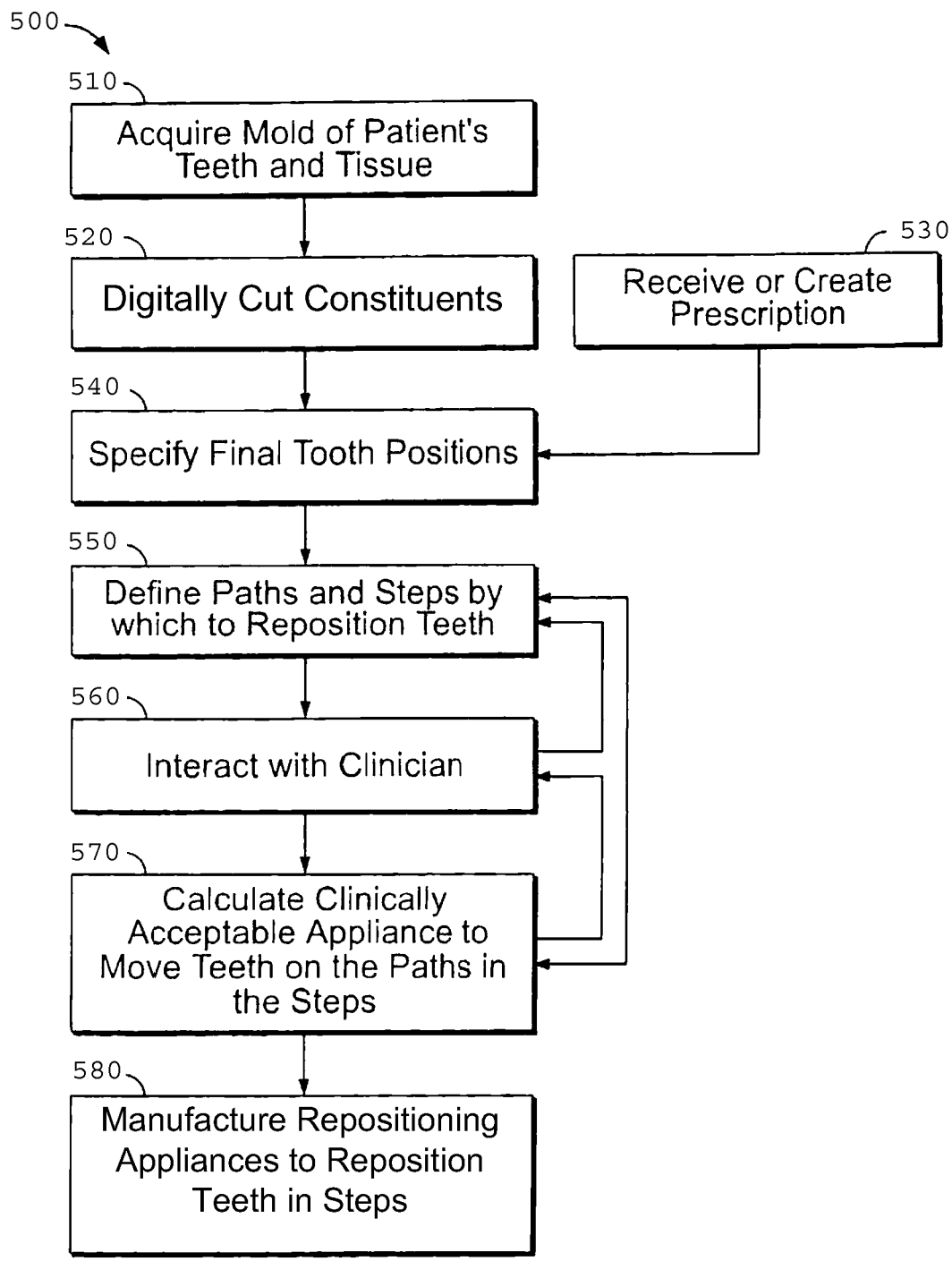
FIG. 5 illustrates an exemplary process for defining and generating repositioning appliances for orthodontic treatment in one aspect.
Figure 6:
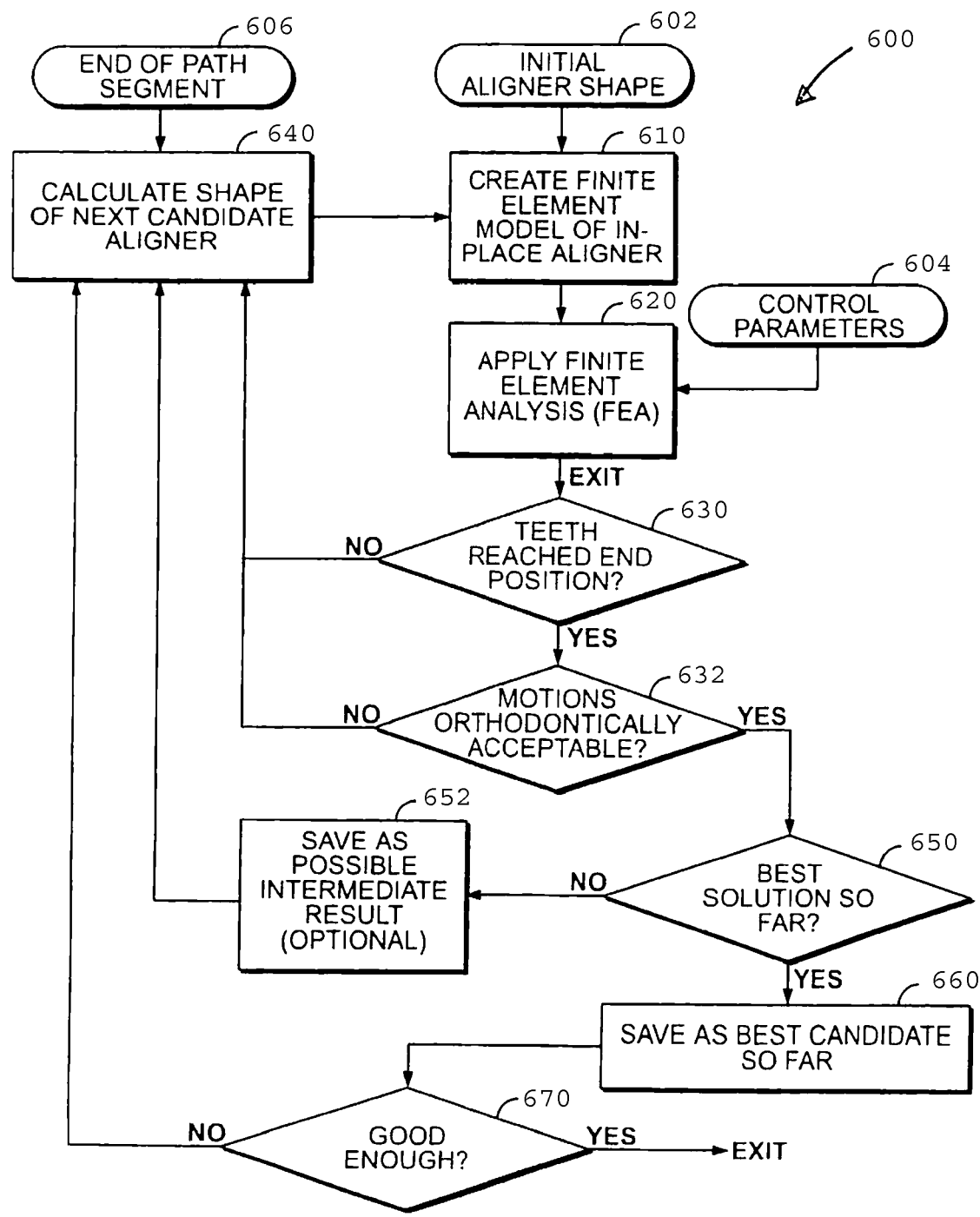
FIG. 6 illustrates a process implementing the appliance calculation of FIG. 5 in one aspect.

FIG. 5 illustrates the general flow of an exemplary process 500 for defining and generating repositioning appliances for orthodontic treatment of a patient. The computational steps of the process are advantageously implemented as computer program modules for execution on one or more conventional digital computers.

As an initial step, a mold or a scan of patient's teeth or mouth tissue is acquired (510). This step generally involves taking casts of the patient's teeth and gums, and may in addition or alternately involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents the initial (that is, pretreatment) arrangement of the patient's teeth and other tissues.

The initial digital data set, which may include both raw data from scanning operations and data representing surface models derived from the raw data, is processed to digitally cut the tissue constituents from each other (520). In particular, in this step, data structures that digitally represent individual tooth crowns are produced. Advantageously, digital models of entire teeth are produced, including measured or extrapolated hidden surfaces and root structures.

The desired target position of the teeth, that is, the desired and intended end result of orthodontic treatment, can be received from a clinician in the form of a prescription, can be calculated from basic orthodontic principles, or can be extrapolated computationally from a clinical prescription (530). With a specification of the desired target positions of the teeth and a digital representation of the teeth themselves, the target position and surface geometry of each tooth can be specified (540) to form a complete model of the teeth at the desired end of treatment. Generally, in this step, the position of every tooth is specified. The result of this step is a set of digital data structures that represents an orthodontically correct repositioning of the modeled teeth relative to presumed-stable tissue. The teeth and tissue are both represented as digital data.

Having both a beginning position and a target position for each tooth, the process next defines a tooth path for the motion of each tooth. In one embodiment, the tooth paths are optimized in the aggregate so that the teeth are moved in the quickest fashion with the least amount of round-tripping to bring the teeth from their initial positions to their desired target positions. (Round-tripping is any motion of a tooth in any direction other than directly toward the desired target position. Round-tripping is sometimes necessary to allow teeth to move past each other.) The tooth paths are segmented. The segments are calculated so that each tooth's motion within a segment stays within threshold limits of linear and rotational translation. In this way, the end points of each path segment can constitute a clinically viable repositioning, and the aggregate of segment end points constitute a clinically viable sequence of tooth positions, so that moving from one point to the next in the sequence does not result in a collision of teeth.

The threshold limits of linear and rotational translation are initialized, in one implementation, with default values based on the nature of the appliance to be used. More individually tailored limit values can be calculated using patient-specific data. The limit values can also be updated based on the result of an appliance-calculation (570), which may determine that at one or more points along one or more tooth paths, the forces that can be generated by the appliance on the then-existing configuration of teeth and tissue is incapable of effecting the repositioning that is represented by one or more tooth path segments. With this information, the subprocess defining segmented paths (550) can recalculate the paths or the affected subpaths.

At various stages of the process, and in particular after the segmented paths have been defined, the process can, and generally will, interact with a clinician responsible for the treatment of the patient (560). Clinician interaction can be implemented using a client process programmed to receive tooth positions and models, as well as path information from a server computer or process in which other steps of process 500 are implemented. The client process is advantageously programmed to allow the clinician to display an animation of the positions and paths and to allow the clinician to reset the target positions of one or more of the teeth and to specify constraints to be applied to the segmented paths. If the clinician makes any such changes, the subprocess of defining segmented paths (550) is performed again.

The segmented tooth paths and associated tooth position data are used to calculate clinically acceptable appliance configurations (or successive changes in appliance configuration) that will move the teeth on the defined treatment path in the steps specified by the path segments (570). Each appliance configuration represents a step along the treatment path for the patient. The steps are defined and calculated so that each discrete position can follow by straight-line tooth movement or simple rotation from the tooth positions achieved by the preceding discrete step and so that the amount of repositioning required at each step involves an orthodontically optimal amount of force on the patient's dentition. As with the path definition step, this appliance calculation step can include interactions and even iterative interactions with the clinician (560). The operation of a process 600 implementing this step is described more fully below.

Having calculated appliance definitions, the process 500 can proceed to the manufacturing step (580) in which appliances defined by the process are manufactured, or electronic or printed information is produced that can be used by a manual or automated process to define appliance configurations or changes to appliance configurations.

FIG. 6 illustrates a process 600 implementing the appliance-calculation step (570) (FIG. 5) for polymeric shell aligners of the kind described in above-mentioned U.S. Pat. No. 5,975,893. Inputs to the process include an initial aligner shape 602, various control parameters 604, and a desired end configuration for the teeth at the end of the current treatment path segment 606. Other inputs include digital models of the teeth in position in the jaw, models of the jaw tissue, and specifications of an initial aligner shape and of the aligner material. Using the input data, the process creates a finite element model of the aligner, teeth and tissue, with the aligner in place on the teeth 610. Next, the process applies a finite element analysis to the composite finite element model of aligner, teeth and tissue 620. The analysis runs until an exit condition is reached, at which time the process evaluates whether the teeth have reached the desired end position for the current path segment, or a position sufficiently close to the desired end position 630. If an acceptable end position is not reached by the teeth, the process calculates a new candidate aligner shape 640. If an acceptable end position is reached, the motions of the teeth calculated by the finite elements analysis are evaluated to determine whether they are orthodontically acceptable 632. If they are not, the process also proceeds to calculate a new candidate aligner shape 640. If the motions are orthodontically acceptable and the teeth have reached an acceptable position, the current aligner shape is compared to the previously calculated aligner shapes. If the current shape is the best solution so far 650, it is saved as the best candidate so far 660. If not, it is saved in an optional step as a possible intermediate result 652. If the current aligner shape is the best candidate so far, the process determines whether it is good enough to be accepted 670. If it is, the process exits. Otherwise, the process continues and calculates another candidate shape 640 for analysis.

The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, Calif. For creating finite element models and analyzing them, program products from a number of vendors can be used, including the PolyFEM product available from CADSI of Coralville, Iowa, the Pro/Mechanica simulation software available from Parametric Technology Corporation of Waltham, Mass., the I-DEAS design software products available from Structural Dynamics Research Corporation (SDRC) of Cincinnati, Ohio, and the MSC/NASTRAN product available from MacNeal-Schwendler Corporation of Los Angeles, Calif.

Referring back to FIG. 4, in some instances, correcting certain malocclusions of a patient's bite set and tooth position through the process of the use of the polymeric shell appliance system as described above, may cause the polymeric shell appliance system process to perform at lower than optimal efficiency. In these instances, the polymeric appliance based treatment system may be supplemented with an additional or supplementary orthodontic treatment process (420) occurring before, after or during the polymeric appliance based treatment. One or more of such supplementary treatment processes may include, among others, fixed orthodontic appliance based treatment process, treatments based on using elastics or other removable appliances, or oral surgery, among others.

In one embodiment of the present disclosure, the target tooth position as determined by the routines described in conjunction with FIGS. 5 and 6, may be displayed both separate and in conjunction with the applied results from a simulation of the supplementary orthodontic treatment process (430) (FIG. 4). This allows for the polymeric shell appliances to be manufactured for the treatment of only certain chosen malocclusions of the patient's teeth, while the supplementary treatment is designed to treat the remainder of the corrections. Additionally, this allows the patient and treating dental professional to view the target results from both the polymeric shell appliance system procedure alone, and in conjunction with the selected supplementary treatment process.

Furthermore, the target results from the polymeric shell appliance system treatment process may be used to report what changes may be desired (440) (FIG. 4) in terms of millimeters, degrees, and direction of change as a result of the supplementary treatment process. Given multiple treatment modalities, whether executed, initiated or performed sequentially or concurrently, the target of one treatment mode may be visualized as being independent from the target of the second or another treatment mode, each of which may be analyzed independently with respect to the planned or desired dental or skeletal movement. The combination of these treatments may also be visualized in combination, such that the total movement planned may be computed or determined. Furthermore, adjustments to one treatment mode may be visualized in the combined visualization mode, such that the potential impact of modifications to one treatment mode may be viewed in conjunction with or in view of the combined treatment. In one aspect, alterations to one or more treatment modes may be iterated until, for example, two or more targets may be compatible towards the desired target.

Once the patient and treating professional are satisfied with the results of the simulation as displayed on, for example, a computer display screen, the polymeric shell appliances may be fabricated (450) (FIG. 4) and the supplementary treatment may be applied (460) (FIG. 4). In one aspect, the patient treatment approach described above may include two or more different types of treatments. That is, in one aspect, two or more different orthodontic treatment techniques may be implemented in accordance with embodiments of the present disclosure. Furthermore, in still another aspect, the end or conclusion of one treatment process may coincide or define the beginning or start of another treatment process. That is, with multiple treatment process implemented in conjunction with the various embodiments of the present disclosure, the starting point and end point of each treatment process may be defined by the respective end point or starting point of the subsequent treatment process. For example, in accordance with an orthodontic treatment process which includes two different types of treatments, the beginning of the second treatment type is defined by the end or conclusion of the first treatment type. Moreover, in aspect of the present disclosure, the patient treatment approach may include multiple treatment types that are repeated with equal frequency during the course of the treatment, or alternatively, one or more treatment types repeated more frequently than another one or more treatment types.

Figure 7:
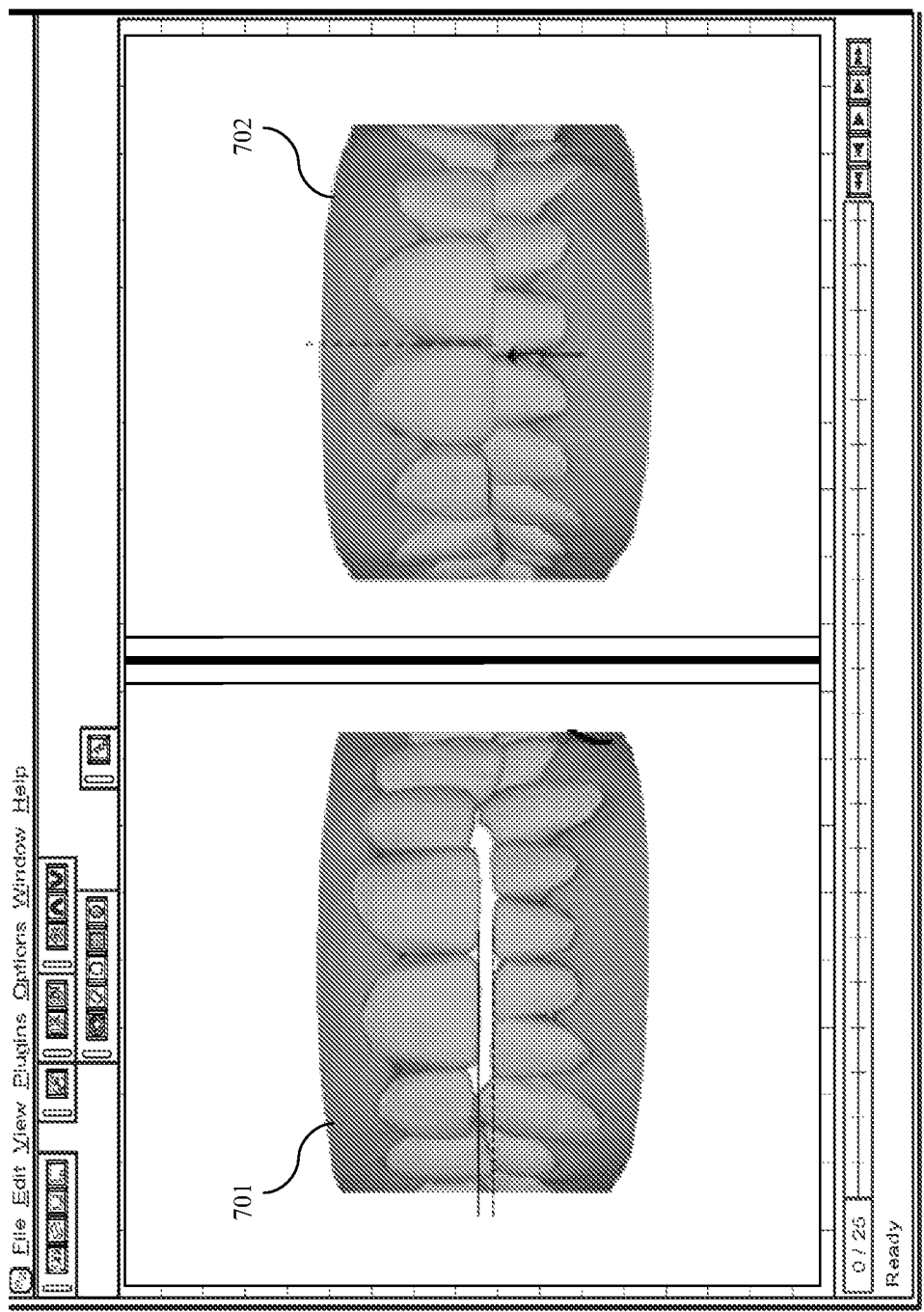
FIG. 7 illustrates simulated output display based on the multiple treatment processes in a further aspect.

FIG. 7 illustrates simulated output display based on the multiple treatment processes in a further aspect. The software program product described in conjunction with FIGS. 4-6 for displaying the simulated output from the polymeric shell appliance system process and the supplementary orthodontic treatment process, may include a multi-screen display. Referring to FIG. 7, the multi-screen display 700 may be used to display the target results from the polymeric shell appliance system procedure alone 701 and the target results from the polymeric shell appliance system procedure in conjunction with the supplementary orthodontic procedure results 702. The side-by-side representation 700 may allow for the patient and treating dental professional to visualize the effects of the supplementary procedure compared to the results from the initial polymeric shell appliance system procedure alone.

Figure 8:
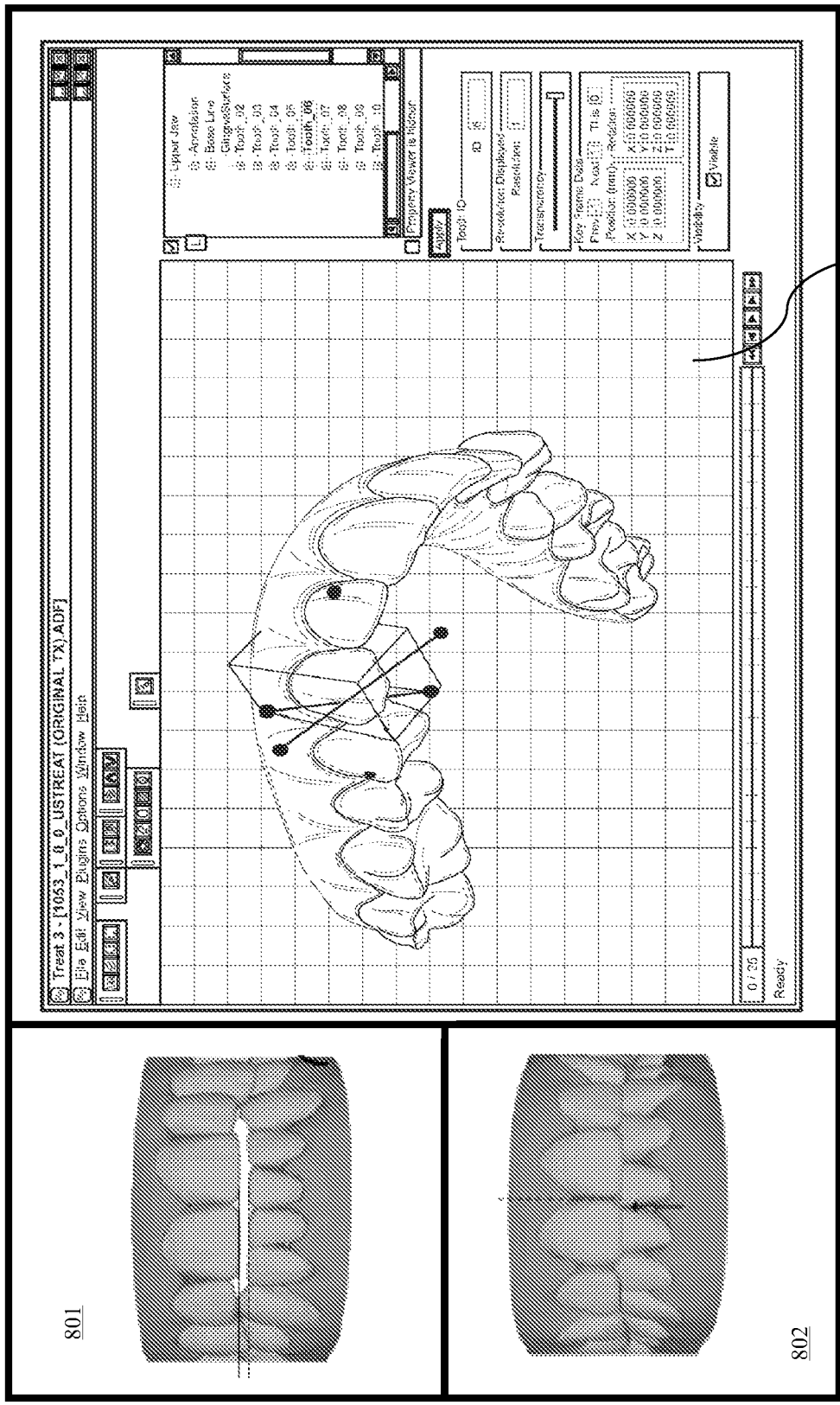
FIG. 8 illustrates a display of an alternate bite relationship viewing window incorporated into the software employed in the processes of FIGS. 4-6 in one aspect.

FIG. 8 illustrates one embodiment of the present disclosure, wherein an alternate bite relationship viewing window is incorporated into the software employed in the processes depicted in FIGS. 4-6. Referring to FIG. 8, one window of the display may be a display of the target result tooth parameters after the polymeric shell appliance system procedure only 801, another window may be of the target result tooth parameters after the polymeric shell appliance system procedure in conjunction with a supplementary orthodontic procedure 802, and a third window may be an editable window, wherein the orthodontist or treating professional may, for example, position the upper or lower or both arches into a new position or change individual tooth positions 803.

A data set including, among others, changes in terms of millimeters, degrees, and direction of change between the target results from the polymeric shell appliance system procedure only as depicted in window 801 compared to the target results from the polymeric shell appliance system in conjunction with a supplementary orthodontic procedure as depicted in window 802, may also be calculated and displayed. This allows for accurate determination of the scope of the surgical or other supplementary procedure to be applied to the patient's teeth. While a three-window display is depicted in FIG. 8, it should be noted that any number of display windows may displayed simultaneously, and each window may be used to display data for any moment in time of the chosen procedure(s), may be used to display a single tooth, a plurality of teeth, a single jaw, or an entire bite set, may be displayed at any number of different viewing angles, and may be used for any applicable treatment step described herein, and each window may be used for viewing only purposes or for editing purposes.

Referring still to FIG. 8, in one embodiment of the present disclosure, individual tooth positions may be modified in window 803. Window 803 may allow for the user or treating professional to display individual teeth, a plurality of teeth, or an entire jaw. Teeth position modifications made in window 803 may be displayed in both windows 801 and 802. The polymeric shell appliance system is one method for treating the position and geometry of individual teeth, and as such, modifications in individual tooth positions is incorporated into the polymeric shell appliance system part of the overall procedure, and therefore does effect the manufacturing process of the polymeric shell appliances. Additionally, since window 802 displays both the target results after the polymeric shell appliance system process and a supplementary procedure, changes made to individual tooth positions also is displayed in window 802. Since changes in the individual tooth positions may affect the scope of the supplementary orthodontic procedure, the data set indicating the changes in terms of millimeters, degrees, and direction of change is updated.

Still referring to FIG. 8, in yet another embodiment of the present disclosure, when the position of the upper or lower or both arches of a patient are positioned by the treating professional in window 803, the changes are not applied to the target result tooth parameters shown in window 801. This implies that the polymeric shell appliances are designed for manufacture without taking into account this change. However, the change would appear in window 802 as a result of a supplementary orthodontic treatment process. This is due to the fact that changing positions of the arches of a patient may lower the efficiency of the polymeric shell appliances system process, and therefore may it may be preferable to treat such conditions through the use of a supplementary procedure, such as oral surgery. The change in position of the upper or lower or both jaws depicted in window 802 in relation to the target result depicted in window 801 may be displayed as a data set including, among others, changes in terms of millimeters, degrees, and direction of change. This allows for accurate determination of the scope of the surgical or other supplementary procedure to be applied to the patient's teeth.

The software program product and methods depicted in FIGS. 7-8 and described above may be applied as a new software program product, or as a feature or update to the existing ClinCheck® software, a part of the Invisalign® System by Align Technology, Inc., or as a feature or update to any other comparable existing software program product or system.

Figure 9:
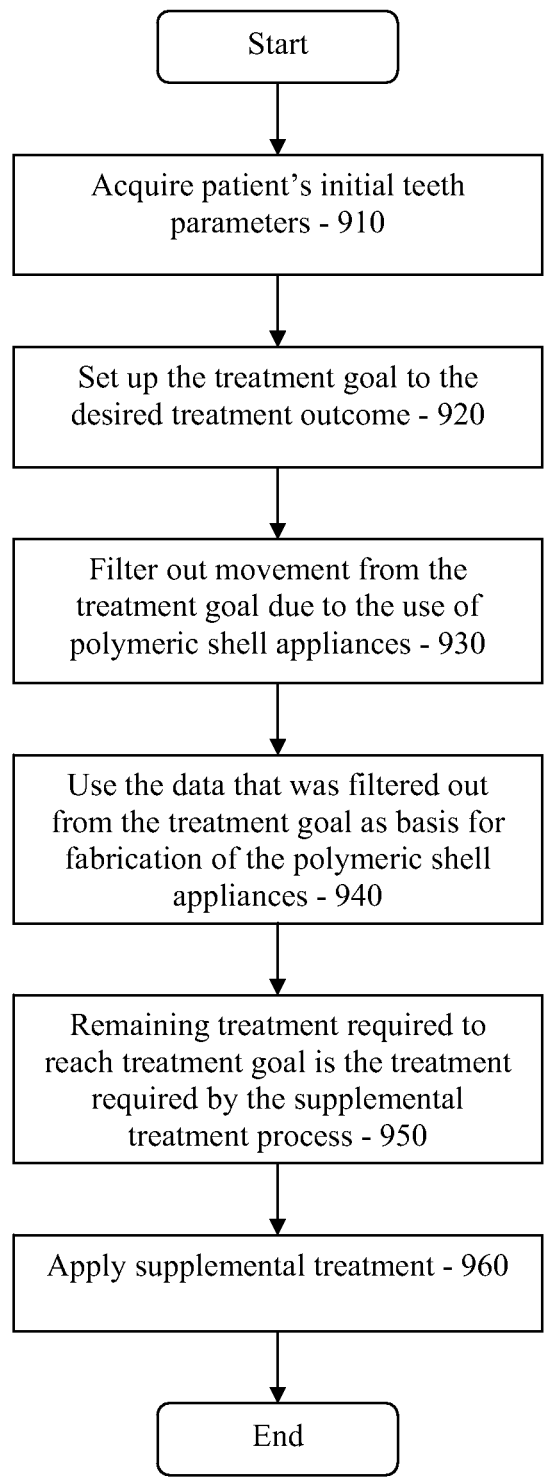
FIG. 9 illustrates a process for using multiple treatment types for orthodontic treatment in another aspect.

FIG. 9 illustrates a process for using multiple treatment types for orthodontic treatment in another aspect. Referring to the FIG., after acquiring the patient's initial teeth parameters (910), the desired treatment goal is setup to the desired treatment outcome (920). Thereafter, movement from the treatment goal resulting from the use of polymeric shell appliances is filtered out (930), and the filtered data set is used as the basis for the fabrication process for the fabrication of the polymeric shell appliances (940). Referring again to FIG. 9, one or more supplemental treatment process (which may be different from the treatment base on the polymeric shell appliances) is determined for the remaining treatment necessary to reach the treatment goal (950), and thereafter, the supplementary treatment is applied for patient treatment (960).

Figure 10:
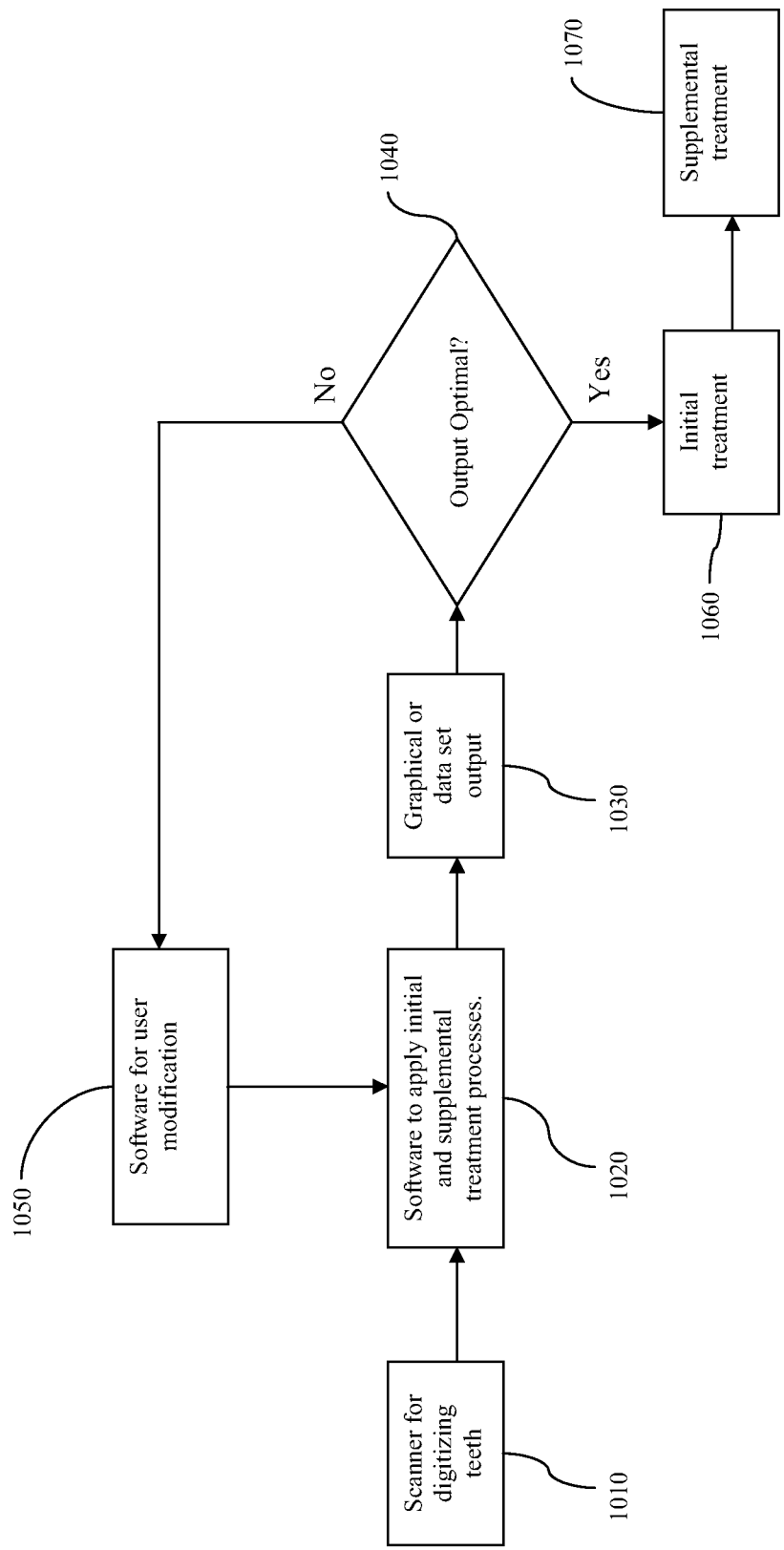
FIG. 10 illustrates a system for applying two treatment procedures for treating malocclusion of a patient's teeth.

FIG. 10 illustrates a general system for applying two treatment procedures for treating malocclusion of a patient's teeth. Referring to FIG. 10, in order to simulate treatment of a patient's teeth, a digital scan of the initial tooth parameters of the patient's teeth is needed. This may be achieved by the use of a scanner (1010), which may be of the type including, but not limited to, X-ray or MRI. The digital initial tooth parameters are loaded into a software program product (1020), which applies chosen initial and supplementary treatment processes to the initial teeth parameters.

The software program product may be configured to simulate the effects of the chosen treatment processes, and outputs the target results. The output may be displayed as either a graphical representation or a data set or a combination thereof (1030). The treating dental professional may inspect the output of the target results, which, in one embodiment of the present disclosure, is a display of both the results from the chosen initial treatment process only and the initial treatment process in conjunction with the supplementary treatment process, and decide if the output is an optimal occlusion (1040), or positioning of the teeth. In the case that the output is not of optimal result, the treating professional may edit the desired results (1050) and feed the new data back into the software program (1020) to update the simulation. Again, the results are displayed (1030) for the treating professional's review, and if necessary, more alterations are made (1050).

Once the treating professional is satisfied with the results of the simulation, the initial treatment procedure begins (1060). This may include, among others, the fabrication of a plurality of polymeric shell appliances based on the software program's data sets as described in FIGS. 5-6 above, the fabrication of other removable orthodontic appliances, the installation of a fixed bracket and arch wire orthodontic system, such as braces, or an oral surgery. At a pre-determined point before, during, or after the initial treatment procedure, a supplementary treatment procedure is implemented (1070). This may also include, among others, the fabrication of a plurality of polymeric shell appliances based on the software program's data sets as described in FIGS. 5-6 above, the fabrication of other removable orthodontic appliances, the installation of a fixed bracket and arch wire orthodontic system, such as braces, or an oral surgery. At the conclusion of the implementation of the shown system and methods incorporated therein, the target occlusion of the patient's teeth will be at the previously outputted results (1030) calculated and shown by the simulation (1020).

While the above methods and systems describe embodiments of various processes of an initial polymeric shell appliance system procedure being followed by a single supplementary orthodontic procedure, it is noted that any number of supplementary orthodontic procedures may be used. It is also noted that the supplementary orthodontic procedure may be performed before, during, or after the polymeric shell appliance system procedure and displays of each step in the overall process may be shown in the software program.

It is also noted that although a polymeric shell appliance system procedure is the described as one method of initial treatment, any number of other methods, including, but not limited to, fixed orthodontic appliances, such as braces, elastics or other removable appliances, treatments based on palate expansion, use of Class II or Class III appliances, and oral surgery may be the initial treatment method, and among others, polymeric shell appliance system procedures may be used as the supplementary orthodontic treatment procedure. In other words, any combination of orthodontic treatment procedures used to obtain an optimal target patient occlusion or combination of treatment procedures desired by the patient or treating dental professional are included within the scope of the present disclosure. For example, the one or more treatment processes may include the use of polymeric shell aligners using, for example, Invisalign® orthodontic appliances described in further detail in U.S. Pat. No. 5,975,893, the disclosure of which is incorporated by reference for all purposes, in conjunction with one or more other treatment processes discussed above.

In one embodiment of the present disclosure, there is provided positioning the teeth of a patient through the use of polymeric shell aligners in conjunction with a supplementary orthodontic treatment process. With the aid of virtual orthodontics software, two or more proposed treatment goals may be determined. The first of the treatment goals is the aligner treatment goal, or the result of the aligner treatment portion of the orthodontic process being applied to the initial teeth parameters. This treatment goal may be used as the basis for the manufacturing of the polymeric shell aligner appliances. The second or more treatment goals may be configured to reflect the target result after simulations of the supplemental treatment procedures are applied to the post-aligner treatment teeth parameters.

In another aspect, there is provided method and system to effectively simulate more than one proposed treatment goal, while maintaining the Invisalign® based treatment system portion of the treatment separate for fabrication purposes. In this manner, a display output may be provided that illustrate both the target results from the Invisalign® based treatment process, or other treatment process or system, and the results from the supplementary treatment process, and a data set accurately comparing the two results.

Accordingly, a method in one aspect includes receiving digital representations of the initial parameters of a dentition, simulating a first orthodontic treatment process on the digital representations of the initial parameters, displaying a set of output results from the simulation of the first orthodontic treatment process, simulating a second orthodontic treatment process on the output results from the simulation of the first orthodontic treatment process, and displaying a set of output results from the simulation of the second orthodontic treatment process.

In one aspect, the method may include a fabrication process to process one or more orthodontic appliances based at least in part on the output results from the first or second orthodontic processes.

The first orthodontic treatment process may include a polymeric shell appliances system treatment process.

In a further aspect, the second orthodontic treatment process may include a polymeric shell appliances system treatment process.

Further, the fabrication process may include fabricating a plurality of polymeric shell appliances based on the simulation of the first orthodontic treatment process.

Also, the fabrication process may include fabricating a plurality of polymeric shell appliances based on the simulation of the second orthodontic treatment process.

The method in yet another aspect may include modifying the first or second orthodontic treatments before manufacturing one or more orthodontic appliances based at least in part on one or more of the first or second orthodontic treatment processes.

In still another aspect, the method may include displaying the set of output results from the simulation of the first orthodontic treatment process and the set of output results from the simulation of the second orthodontic treatment process simultaneously.

Additionally, the method may include displaying a data set of information for use in the second orthodontic treatment in reference to the output results of the first orthodontic treatment.

Moreover, the first orthodontic treatment process may be different than the second orthodontic treatment process, or alternatively, the first orthodontic treatment process may be the same as the second orthodontic treatment process.

In yet a further aspect, an end point of one of the first orthodontic treatment process or the second orthodontic treatment process may substantially coincide with a beginning point of the other one of the first orthodontic treatment process or the second orthodontic treatment process. That is, in one aspect, the end point or conclusion of one of the first or second orthodontic treatment process may define or coincide with the beginning or the starting point of the other one of the first or second orthodontic treatment process.

The first orthodontic treatment process and the second orthodontic treatment process may include one or more of a palate expansion treatment, a Class II appliance based treatment, a Class II appliance based treatment, a polymeric shell appliance based treatment, a wire and bracket based treatment, or one or more combinations thereof.

A computer program product in accordance with one embodiment may include a medium readable by a computer, the computer readable medium having computer program code adapted to: receive digital representations of the initial parameters of a dentition, simulate a first orthodontic treatment process on the digital representations of the initial parameters, display a set of output results from the simulation of the first orthodontic treatment process, simulate a second orthodontic treatment process on the output results from the simulation of the first orthodontic treatment process, and display a set of output results from the simulation of the second orthodontic treatment process.

In one embodiment, the medium readable by the computer, the computer readable medium having computer program code may be adapted to perform a fabrication process to process one or more orthodontic appliances based at least in part on the output results from the first or second orthodontic processes.

Additionally, the medium readable by the computer, the computer readable medium having computer program code may be adapted to modify the first or second orthodontic treatments before manufacturing one or more orthodontic appliances based at least in part on one or more of the first or second orthodontic treatment processes.

In still another aspect, the medium readable by the computer, the computer readable medium having computer program code may be adapted to display the set of output results from the simulation of the first orthodontic treatment process and the set of output results from the simulation of the second orthodontic treatment process simultaneously.

Still in a further aspect, the medium readable by the computer, the computer readable medium having computer program code may be adapted to display a data set of information for use in the second orthodontic treatment in reference to the output results of the first orthodontic treatment.

Various other modifications and alterations in the structure and method of operation of the present disclosure will be apparent to those skilled in the art without departing from the scope and spirit of the present disclosure. Although the embodiments of the present disclosure has been described in connection with specific embodiments, it should be understood that the embodiments as claimed should not be unduly limited to such specific embodiments. It is intended that the following claims define the scope of the present disclosure and that structures and methods within the scope of these claims and their equivalents be covered thereby.

What is claimed is:

1. A method for creating a visualization of results corresponding to a dental treatment including a first orthodontic treatment process, a second orthodontic treatment process, and a third orthodontic process, wherein said visualization of results is created prior to implementation of said first orthodontic treatment process, said second orthodontic treatment process, or said third orthodontic process dental treatment on a patient, said method comprising:
   receiving digital representations of initial teeth parameters of a dentition, wherein the digital representations comprise a digital set that is digitally cut to represent individual tooth crowns;
   simulating a first orthodontic treatment process on the digital representations of the initial teeth parameters, wherein the simulating the first orthodontic treatment process comprises:
      virtually applying a first chosen treatment to the initial teeth parameters of the dentition;
      displaying a set of output results from the simulation of the first orthodontic treatment process;
   simulating a second orthodontic treatment process on the set of output results from the simulation of the first orthodontic treatment process, wherein the set of output results comprises supplementary initial teeth parameters, and wherein the simulating the second orthodontic treatment process comprises:
      virtually applying a second chosen treatment to the supplementary initial teeth parameters, wherein the first chosen treatment is a different treatment type than the second chosen treatment, wherein the first chosen treatment and second chosen treatment that are virtually applied to, respectively, the initial teeth parameters of the dentition and the supplementary initial teeth parameters of the dentition, comprise virtual geometric representations of forces that are applied to the dentition via the first and second chosen treatment;
   simulating a third orthodontic treatment process on the set of output results from the simulation of the second orthodontic treatment process, wherein the set of output results comprises third initial teeth parameters, and wherein the simulating the third orthodontic treatment process comprises:
      virtually applying a third chosen treatment to the supplementary initial teeth parameters, wherein the first chosen treatment is a different treatment type than the second chosen treatment and the third chosen treatment, wherein the first chosen treatment, second chosen treatment and third chosen treatment that are virtually applied to, respectively, the initial teeth parameters of the dentition, the supplementary initial teeth parameters of the dentition, and the third initial teeth parameters comprise virtual geometric representations of forces that are applied to the dentition via the first chosen treatment, second chosen treatment and third chosen treatment;
   iteratively altering the first orthodontic treatment process, the second orthodontic treatment process, and the third treatment process until compatibility between each of the first, second, and third orthodontic treatment processes occurs towards a planned teeth movement; and
   displaying a set of output results from the simulation of the third orthodontic treatment, and the second orthodontic treatment process simultaneously with the displaying of the set of output results from the simulation of the first orthodontic treatment process, such that said visualization of results corresponding to said dental treatment is available to a treating professional prior to implementation on said patient of said first orthodontic treatment process, said second orthodontic treatment process, or said third orthodontic treatment process.

2. The method of claim 1 wherein a fabrication process to process one or more orthodontic appliances is based at least in part on the output results from the first or second orthodontic processes.

3. The method of claim 2, wherein the fabrication process includes fabricating a plurality of polymeric shell appliances based on the simulation of the first orthodontic treatment process.

4. The method of claim 2, wherein the fabrication process includes fabricating a plurality of polymeric shell appliances based on the simulation of the second orthodontic treatment process.

5. The method of claim 1, wherein the first orthodontic treatment process is a
polymeric shell appliances system treatment process.

6. The method of claim 1, wherein the second orthodontic treatment process is a polymeric shell appliances system treatment process.

7. The method of claim 1, further comprising modifying the first orthodontic treatment process or the second orthodontic treatment process before manufacturing one or more orthodontic appliances based at least in part on one or more of the first orthodontic treatment process or the second orthodontic treatment process.

8. The method of claim 1, further comprising displaying a data set of information for use in the second orthodontic treatment process in reference to the output results of the first orthodontic treatment process.

9. The method of claim 1 wherein the first orthodontic treatment process is different than the second orthodontic treatment process.

10. The method of claim 1 wherein the first orthodontic treatment process is the same as the second orthodontic treatment process.

11. The method of claim 1 wherein an end point of one of the first orthodontic treatment process or the second orthodontic treatment process coincides with a beginning point of the other one of the first orthodontic treatment process or the second orthodontic treatment process.

12. The method of claim 1 wherein the first orthodontic treatment process and the second orthodontic treatment process includes one or more of a palate expansion treatment, a Class II appliance based treatment, a Class II appliance based treatment, a polymeric shell appliance based treatment, a wire and bracket based treatment, or one or more combinations thereof.

13. The method of claim 1, wherein the first chosen treatment comprises a representative use of a polymeric shell appliance, and the second chosen treatment comprises a representative use of a fixed orthodontic appliance.

14. A non-transitory computer readable storage medium having stored thereon, computer-executable instructions that, when executed by a computer, cause the computer to perform a method for creating a visualization of results corresponding to a dental treatment including a first orthodontic treatment process, a second orthodontic treatment process, and a third orthodontic process, wherein said visualization of results is created prior to implementation of said first orthodontic treatment process, said second orthodontic treatment process, or said third orthodontic process dental treatment on a patient, said method comprising:

receiving digital representations of initial teeth parameters of a dentition, wherein the digital representations comprise a digital set that is digitally cut to represent individual tooth crowns;

simulating a first orthodontic treatment process on the digital representations of the initial teeth parameters, wherein the simulating the first orthodontic treatment process comprises:

virtually applying a first chosen treatment to the initial teeth parameters of the dentition;

displaying a set of output results from the simulation of the first orthodontic treatment process;

simulating a second orthodontic treatment process on the set of output results from the simulation of the first orthodontic treatment process, wherein the set of output results comprises supplementary initial teeth parameters, and wherein the simulating the second orthodontic treatment process comprises:

virtually applying a second chosen treatment to the supplementary initial teeth parameters, wherein the first chosen treatment is a different treatment type than the second chosen treatment, wherein the first chosen treatment and second chosen treatment that are virtually applied to, respectively, the initial teeth parameters of the dentition and the supplementary initial teeth parameters of the dentition, comprise virtual geometric representations of forces that are applied to the dentition via the first and second chosen treatment;

simulating a third orthodontic treatment process on the set of output results from the simulation of the second orthodontic treatment process, wherein the set of output results comprises third initial teeth parameters, and wherein the simulating the third orthodontic treatment process comprises:

virtually applying a third chosen treatment to the supplementary initial teeth parameters, wherein the first chosen treatment is a different treatment type than the second chosen treatment and the third chosen treatment, wherein the first chosen treatment, second chosen treatment and third chosen treatment that are virtually applied to, respectively, the initial teeth parameters of the dentition, the supplementary initial teeth parameters of the dentition, and the third initial teeth parameters comprise virtual geometric representations of forces that are applied to the dentition via the first chosen treatment, second chosen treatment and third chosen treatment;

iteratively altering the first orthodontic treatment process, the second orthodontic treatment process, and the third treatment process until compatibility between each of the first, second, and third orthodontic treatment processes occurs towards a planned teeth movement; and displaying a set of output results from the simulation of the third orthodontic treatment, and the second orthodontic treatment process simultaneously with the displaying of the set of output results from the simulation of the first orthodontic treatment process, such that said visualization of results corresponding to said dental treatment is available to a treating professional prior to implementation on said patient of said first orthodontic treatment process, said second orthodontic treatment process, or said third orthodontic treatment process.

15. The non-transitory computer readable storage medium of claim 14, wherein the method further comprises:

performing a fabrication process to process one or more orthodontic appliances is based at least in part on the output results from the first or second orthodontic processes.

16. The non-transitory computer readable storage medium of claim 15, wherein the fabrication process includes fabricating a plurality of polymeric shell appliances based on the simulation of the first orthodontic treatment process.

17. The non-transitory computer readable storage medium of claim 15, wherein the fabrication process includes fabricating a plurality of polymeric shell appliances based on the simulation of the second orthodontic treatment process.

18. The non-transitory computer readable storage medium of claim 14, wherein the first orthodontic treatment process is a polymeric shell appliances system treatment process.

19. The non-transitory computer readable storage medium of claim 14, wherein the second orthodontic treatment process is a polymeric shell appliances system treatment process.

20. The non-transitory computer readable storage medium of claim 14, wherein the method further comprises:

modifying the first orthodontic treatment process or the second orthodontic treatment process before manufacturing one or more orthodontic appliances based at least in part on one or more of the first orthodontic treatment process or the second orthodontic treatment process.

21. The non-transitory computer readable storage medium of claim 14, wherein the method further comprises:

displaying a data set of information for use in the second orthodontic treatment process in reference to the output results of the first orthodontic treatment process.

22. The non-transitory computer readable storage medium of claim 14, wherein the first orthodontic treatment process is different than the second orthodontic treatment process.

23. The non-transitory computer readable storage medium of claim 14, wherein the first orthodontic treatment process is the same as the second orthodontic treatment process.

24. The non-transitory computer readable storage medium of claim 14, wherein an end point of one of the first orthodontic treatment process or the second orthodontic treatment process coincides with a beginning point of the other one of the first orthodontic treatment process or the second orthodontic treatment process.

25. The non-transitory computer readable storage medium of claim 14, wherein the first orthodontic treatment process and the second orthodontic treatment process includes one or more of a palate expansion treatment, a Class 11 appliance based treatment, a Class II appliance based treatment, a polymeric shell appliance based treatment, a wire and bracket based treatment, or one or more combinations thereof.

26. The non-transitory computer readable storage medium of claim 14, wherein the first chosen treatment comprises a representative use of a polymeric shell appliance, and the second chosen treatment comprises a representative use of a fixed orthodontic appliance.

27. A method for creating a visualization of results corresponding to a dental treatment including a first orthodontic treatment process and a second orthodontic process, wherein said visualization of results is created prior to implementation of said first orthodontic treatment process or said second orthodontic process on a patient, said method comprising:
receiving digital representations of initial teeth parameters of a dentition, wherein the digital representations comprise a digital set that is digitally cut to represent individual tooth crowns;
simulating a first orthodontic treatment process on the digital representations of the initial teeth parameters, wherein the simulating the first orthodontic treatment process comprises:
virtually applying a first chosen treatment to the initial teeth parameters of the dentition;
displaying a set of output results from the simulation of the first orthodontic treatment process;
simulating a second orthodontic treatment process on the set of output results from the simulation of the first orthodontic treatment process, wherein the set of output results comprises supplementary initial teeth parameters, and wherein the simulating the second orthodontic treatment process comprises:
virtually applying a second chosen treatment to the supplementary initial teeth parameters, wherein the first chosen treatment is a different treatment type than the second chosen treatment, wherein the first chosen treatment and second chosen treatment that are virtually applied to, respectively, the initial teeth parameters of the dentition and the supplementary initial teeth parameters of the dentition, comprise virtual geometric representations of forces that are applied to the dentition via the first and second chosen treatment;
iteratively altering the first orthodontic treatment process and the second orthodontic treatment process until compatibility between each of the first and second orthodontic treatment processes occurs towards a planned teeth movement; and
displaying a set of output results from the simulation of the second orthodontic treatment process simultaneously with the displaying of the set of output results from the simulation of the first orthodontic treatment process, such that said visualization of results corresponding to said dental treatment is available to a treating professional prior to implementation on said patient of either said first orthodontic treatment process or said second orthodontic treatment process.

28. The method of claim 27 wherein a fabrication process to process one or more orthodontic appliances is based at least in part on the output results from the first or second orthodontic processes.

29. The method of claim 28, wherein the fabrication process includes fabricating a plurality of polymeric shell appliances based on the simulation of the first orthodontic treatment process.

30. The method of claim 28, wherein the fabrication process includes fabricating a plurality of polymeric shell appliances based on the simulation of the second orthodontic treatment process.

31. The method of claim 27, wherein the first orthodontic treatment process is a
polymeric shell appliances system treatment process.

32. The method of claim 27, wherein the second orthodontic treatment process is a polymeric shell appliances system treatment process.

33. The method of claim 27 wherein the first orthodontic treatment process is different than the second orthodontic treatment process.

34. The method of claim 27 wherein the first orthodontic treatment process is the same as the second orthodontic treatment process.

* * * * *